(12) United States Patent
Smith et al.

(10) Patent No.: US 7,462,189 B2
(45) Date of Patent: Dec. 9, 2008

(54) INTEGRATED LUMBAR COMBINED VARIABLE ANGULAR DISTRACTION STRUCTURE

(75) Inventors: Norman A. Smith, Alpharetta, GA (US); Carlos Becerra, Atlanta, GA (US); Shelly O'Neil-Flemming, Marietta, GA (US)

(73) Assignee: North American Medical Corporation, Marietta, GA (US)

( * ) Notice: Subject to any disclaimer, the term of this patent is extended or adjusted under 35 U.S.C. 154(b) by 615 days.

(21) Appl. No.: 11/175,684

(22) Filed: Jul. 6, 2005

(65) Prior Publication Data

US 2006/0015145 A1 Jan. 19, 2006

Related U.S. Application Data

(60) Provisional application No. 60/586,198, filed on Jul. 6, 2004.

(51) Int. Cl.
- *A61F 5/00* (2006.01)
- *A61H 1/00* (2006.01)
- *A61H 1/02* (2006.01)
- *A61H 5/00* (2006.01)

(52) U.S. Cl. ............ 606/237; 601/24; 602/32; 602/33

(58) Field of Classification Search ............ 601/23, 601/24, 26; 606/237, 241, 242; 602/32–35, 602/38, 39; 128/870; 5/648, 650
See application file for complete search history.

(56) References Cited

U.S. PATENT DOCUMENTS

| | | | |
|---|---|---|---|
| 3,134,379 A * | 5/1964 | Nightingale | 602/32 |
| 4,236,265 A | 12/1980 | Carradine | |
| 4,579,109 A | 4/1986 | Lundblad | |
| 4,583,532 A * | 4/1986 | Jones | 602/32 |
| 4,627,423 A | 12/1986 | Kampner | |
| 5,052,378 A | 10/1991 | Chitwood | |
| 5,094,228 A | 3/1992 | Reinert | |
| 5,217,488 A * | 6/1993 | Wu | 606/241 |
| 5,308,359 A | 5/1994 | Lossing | |
| 5,320,641 A | 6/1994 | Riddle et al. | |
| 5,462,518 A * | 10/1995 | Hatley et al. | 602/36 |
| 5,672,157 A | 9/1997 | Gallagher et al. | |
| 5,830,169 A * | 11/1998 | Pierce | 602/32 |
| 5,967,999 A * | 10/1999 | Hulicsko et al. | 602/32 |

(Continued)

FOREIGN PATENT DOCUMENTS

RU 2085172 C1 * 7/1997

*Primary Examiner*—Justine R Yu
*Assistant Examiner*—Kristen C Matter
(74) *Attorney, Agent, or Firm*—Bryan W. Bockhop; Bockhop & Associates, LLC

(57) ABSTRACT

A spinal treatment apparatus for applying a force to a patient includes a base portion, a telescoping support, a spinal distraction device and an actuator. The telescoping support is mounted on the base portion and includes a bottom member and a top member. The top member is engaged with the bottom member so that the top member has a retracted position and an extended position. The telescoping support is capable of withstanding a force, corresponding to the spinal treatment force, imparted on the top member, while in both the retracted position and the extended position. The spinal distraction device is mounted on the top member and applies the spinal treatment force to the patient. The actuator moves the top member vertically relative to the bottom member.

3 Claims, 4 Drawing Sheets

U.S. PATENT DOCUMENTS

| | | |
|---|---|---|
| 6,152,950 A | 11/2000 | Shealy et al. |
| 6,638,299 B2 | 10/2003 | Cox |
| 6,899,690 B2 | 5/2005 | Saunders et al. |
| 6,986,181 B2 * | 1/2006 | Murphy et al. ................ 5/648 |

* cited by examiner

INTEGRATED LUMBAR COMBINED VARIABLE ANGULAR DISTRACTION STRUCTURE

CROSS-REFERENCE TO RELATED APPLICATION(S)

This application claims the benefit of U.S. Provisional Patent Application Ser. No. 60/586,198, filed Jul. 6, 2004, the entirety of which is hereby incorporated herein by reference.

BACKGROUND OF THE INVENTION

1. Field of the Invention

The present invention relates to spinal treatment systems and, more specifically, to a spinal treatment system that includes an integrated variable angular distraction structure.

2. Description of the Prior Art

Pain in the lumbosacral spine is the most common of all pain complaint. Lumbosacral spine pain causes loss of work and is the single most common cause of disability in persons under 45 years of age. Back pain problems are described in various well-known references directed to acute lower back problems, and in particular, articles addressing pain management. Treatments for lower back pain include traction-like methods, which are well known for pain relief. Pelvic traction has been used to treat patients with lower back pain for hundreds of years. However, most neurosurgeons and orthopedists have not been enthusiastic about pelvic traction due to concerns over inconsistent results and cumbersome traction equipment to name a few. Simple traction has been known to be highly effective for treating spine pain. More and more clinics have been including traction as part of their treatment approach as the technology has improved over recent years. More recently, spinal decompression treatment has advanced due to the improvement in equipment and treatment results. Traction is generally known as a process of pulling and is typically performed by pulling and holding. Traction for the lumbar portion of the spine is usually applied by a force to pull on the pelvis, or by using a mobilization technique to distract individual joints of the lumbar vertebrae. Decompression means to remove pressure. In terms of spinal treatment, decompression is typically understood to mean a series of pulls, either periodic or non-periodic, that repeatedly pulls and releases a force from a portion of the spine. By repeating the pulling and releasing force from the spine, the muscles relax so as to treat the spine.

As the technology to provide traction and/or decompression for treating lumbosacral spine pain has been developing, equipment used for the treatment has been expanding to include different and more varied mechanical and electrical hardware for a variety of different and specific treatments. In general, the components of the equipment, including a bed, motors, clutches, linear actuators, and computer system, for example, are produced by a variety of vendors and manufacturers. Manufacturers of the final equipment generally produce and/or integrate the hardware prior to delivery of the equipment to treatment clinics. In integrating the equipment, the various components that are used to perform the lumbosacral spine treatment, or other related treatment, are typically arranged in accordance with the design to work as a system, functionally tested, and repackaged for shipping to a treatment facility for installation. One problem that exists for the manufacturer is the time consumption to configure, test, and repackage the equipment for delivery to a treatment facility. While the components are designed to interact with one another functionally, the components are generally structurally separate items. In order to perform the testing of the equipment, the entire assembly must be configured to perform functional testing.

One technique for providing lumbosacral spine treatment has been to apply both a horizontal and angular distraction component for treating the lumbosacral portion of the spine substantially simultaneously. The distraction is performed on patients that are typically in a supine position (i.e., a person lying on his or her back with knees bent at a forty-five degree angle) with the lower spine at a flexion of 0-30 degrees. The use of the distraction technique in both a horizontal and angular component utilizing conventional equipment, however, is limited in that conventional equipment only provides for fixed angular positions during a given treatment. An operator of the equipment, such as a therapist, sets the desired angular distraction for a patient's treatment based on a patient profile. Other or additional treatment requires mechanically repositioning the angular distraction and starting a second treatment on the patient.

Existing spinal treatment systems typically employ a frame to which a distraction unit is mounted. The distraction unit is moveable relative to the frame by being mounted on a track. The frame must be structured to withstand all of the force imparted on it by the distraction unit. Such systems have the disadvantage of having a bulky, fixed-height frame. The fixed height nature of the frame requires space in the entire height of the frame during transport. Furthermore, as the frame is bulky, it is difficult to add an aesthetic exterior around the frame without adding to undesirable bulkiness of the system.

Therefore, there is a need for a spinal treatment system that can be collapsed to a minimum height.

There is also a need for a spinal treatment system that is sufficiently compact to allow the application of an aesthetic exterior while maintaining a relatively compact form.

SUMMARY OF THE INVENTION

The disadvantages of the prior art are overcome by the present invention which, in one aspect, is a spinal treatment apparatus for applying a spinal treatment force to a patient that includes a base portion, a telescoping support, a spinal distraction device and an actuator. The telescoping support is mounted on and extends upwardly from the base portion and includes a bottom member and a top member. The top member is moveably engaged with the bottom member so that the top member has a retracted position and an extended position. The telescoping support is constructed so as to be capable of withstanding a force, corresponding to the spinal treatment force, imparted on the top member, while in both the retracted position and the extended position. The spinal distraction device is mounted on the top member of telescoping support and applies the spinal treatment force to the patient. The actuator moves the top member vertically relative to the bottom member, thereby moving the spinal distraction device to a selected vertical position.

In another aspect, the invention is a spinal treatment apparatus for applying a spinal treatment force to a patient that includes a base portion, a telescoping support, a spinal distraction device, a linear electrical motor, a treatment bed and a counterweight. The telescoping support is mounted on and extends upwardly from the base portion and includes a bottom member and a top member. The top member is moveably engaged with the bottom member so that the top member has a retracted position and an extended position. The telescoping support is constructed so as to be capable of withstanding a force, corresponding to the spinal treatment force, imparted on the top member, while in both the retracted position and the extended position. The spinal distraction device is mounted on the top member of telescoping support and applies the spinal treatment force to the patient. The linear electric motor moves the top member vertically relative to the bottom member, thereby moving the spinal distraction device to a selected vertical position. The linear electrical motor moves the top member vertically relative to the bottom member, thereby moving the spinal distraction device to a selected vertical position. The treatment bed is capable of supporting the patient and is affixed to the bottom member of the telescoping support. The counterweight is affixed to the bottom member of the telescoping support to balance at least a portion of the force imparted on the top member.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1A:
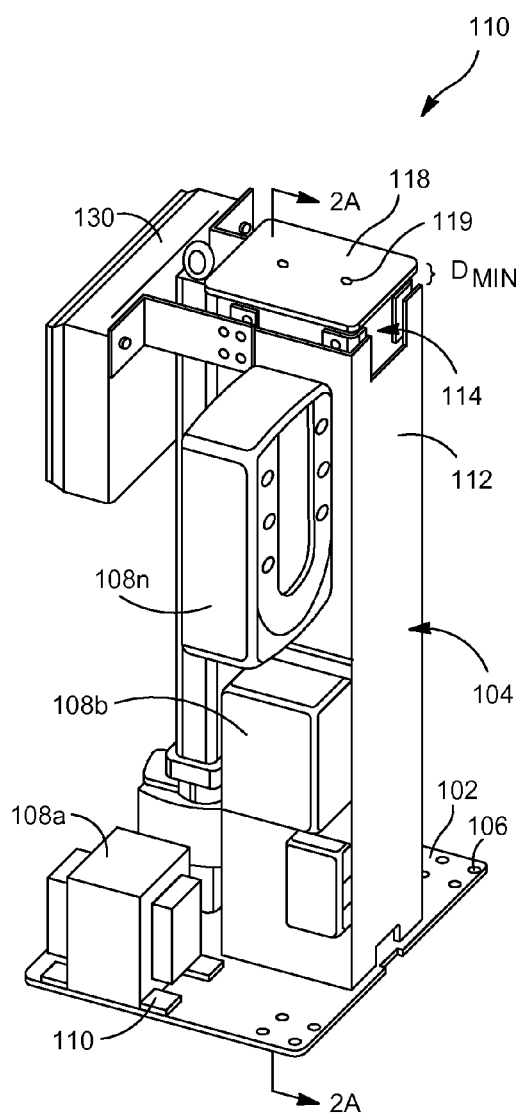
FIG. 1A is a top perspective view of an exemplary structure, in a collapsed state, including a base and telescoping support to mount equipment for performing distraction to a spine of a patient.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIG. 1A, one an exemplary a spinal treatment apparatus 100 (shown in a fully retracted state) includes a base portion 102 and telescoping support 104 extending from the base portion 102 to mount equipment for performing distraction to a spine of a patient. The base 102 may define openings 106 disposed about the base 102 for mounting equipment 108a. Brackets 110 or other coupling devices may be utilized to affix the equipment 108 (collectively, 108 refers herein to equipment 108a-108n) to the base 102. The equipment mounted to the base 102 may include power supplies or other equipment that does not provide functional operations directly related to the treatment of patients.

The telescoping support 104 may be configured as a bottom member 112 with a top member 114 slidably engaged therein. Equipment 108b-108n may be mounted to the base 102 and to the bottom member 112 of the structure 100. The equipment mounted to the bottom member 112 may include electrical or electromechanical equipment, such as a computing device, motors, etc., that provides functional operations during treatment of patients. In one embodiment, the bottom member 112 and the top member 114 may be made of steel conduit (i.e., steel tubing or sheet steel formed so as to have a polygonal cross section) such that the top member 114 fits either inside or outside of the bottom member 112.

The top member 114 may include vertical member supports 116 for a pedestal mount surface 118. Alternately, the pedestal mount surface 118 may be affixed directly to the top member 114. Slide members 120 are coupled to the top member 114. As shown, the top member 114 is fully retracted to a height of Dmin.

Figure 1B:
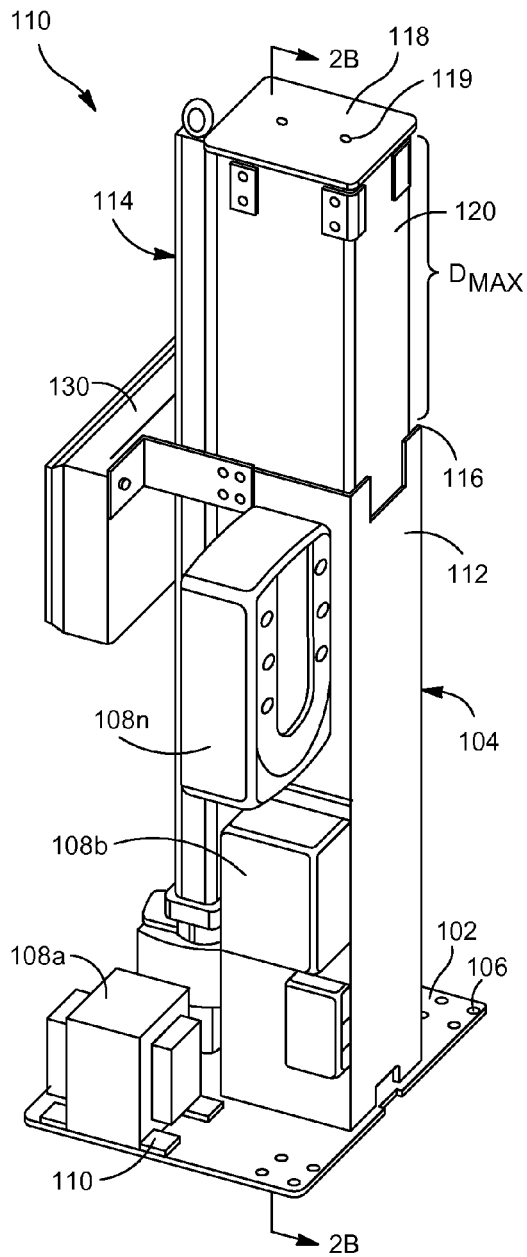
FIG. 1B is a top perspective view of the structure of FIG. 1A, in an extended state.

The pedestal mount surface 118 may include connection points, such as openings 119, to mount a power distraction device (which is shown in more detail in FIG. 3) that may be raised and lowered with the top member 114. FIG. 1B illustrates the exemplary structure in a fully extended state. As shown, the top member 114 is fully extended to a height of Dmax. The height of the top member 114 may be variably adjusted to a height between Dmin and Dmax to move the spinal distraction device 300 to a selected vertical position corresponding to a desired angle of force to be applied to the patient.

Figure 2A:
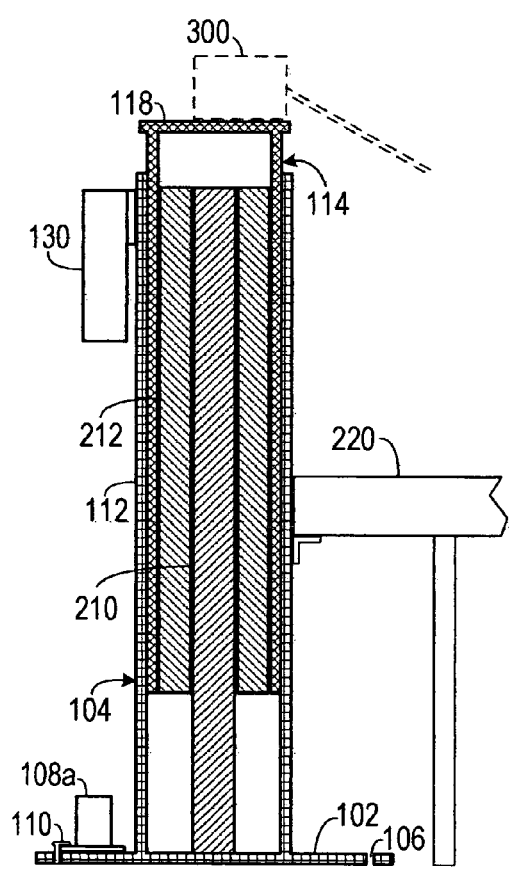
FIG. 2A is a cross sectional view of the structure shown in FIG. 1A, taken along line 2A-2A.
Figure 2B:
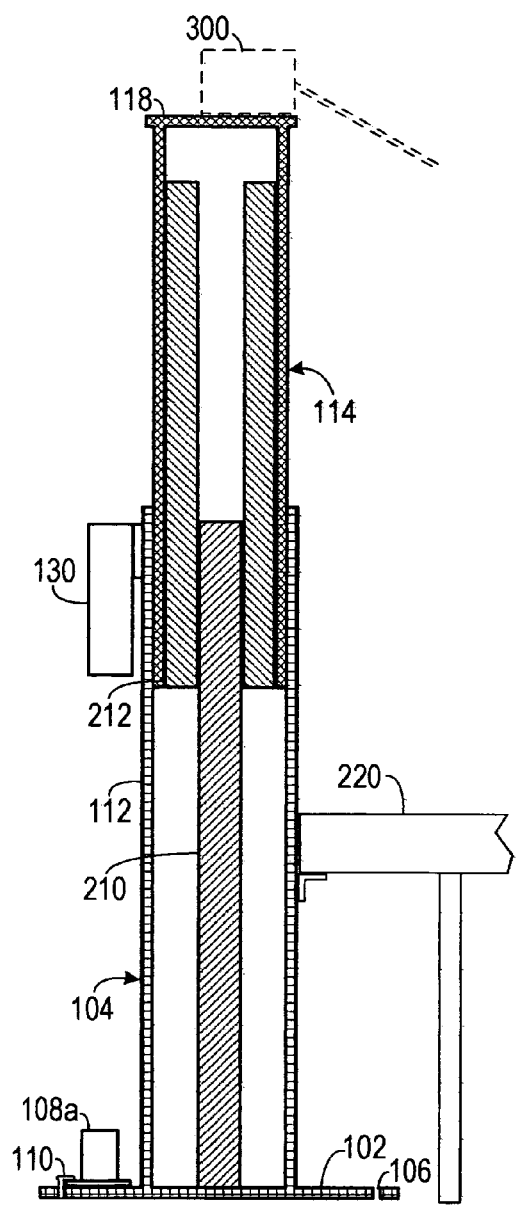
FIG. 2B is a cross sectional view of the structure shown in FIG. 1B, taken along line 2B-2B.

As shown in FIGS. 2A and 2B, an actuator 210 is be coupled the slide members 120 to raise and lower the top member 114. The actuator may be a linear electric motor, a rotatable actuator, a rack and pinion driven by an electric motor, a hydraulic actuator, a pneumatic actuator, or the like. In the case of using a hydraulic or pneumatic actuator, the top member 114 may be configured as a piston within the bottom member 112 as understood in the art. The actuator 210 may be computer controlled to allow for a plurality of subsequent treatment profiles to be applied to a patient during a given treatment session.

A treatment bed 220 may be affixed to the bottom member of the telescoping support and supports the patient during treatment. A counterweight 130 may be affixed to the bottom member of the telescoping support 104 to balance at least a portion of the force imparted on the top member 114.

Figure 3:
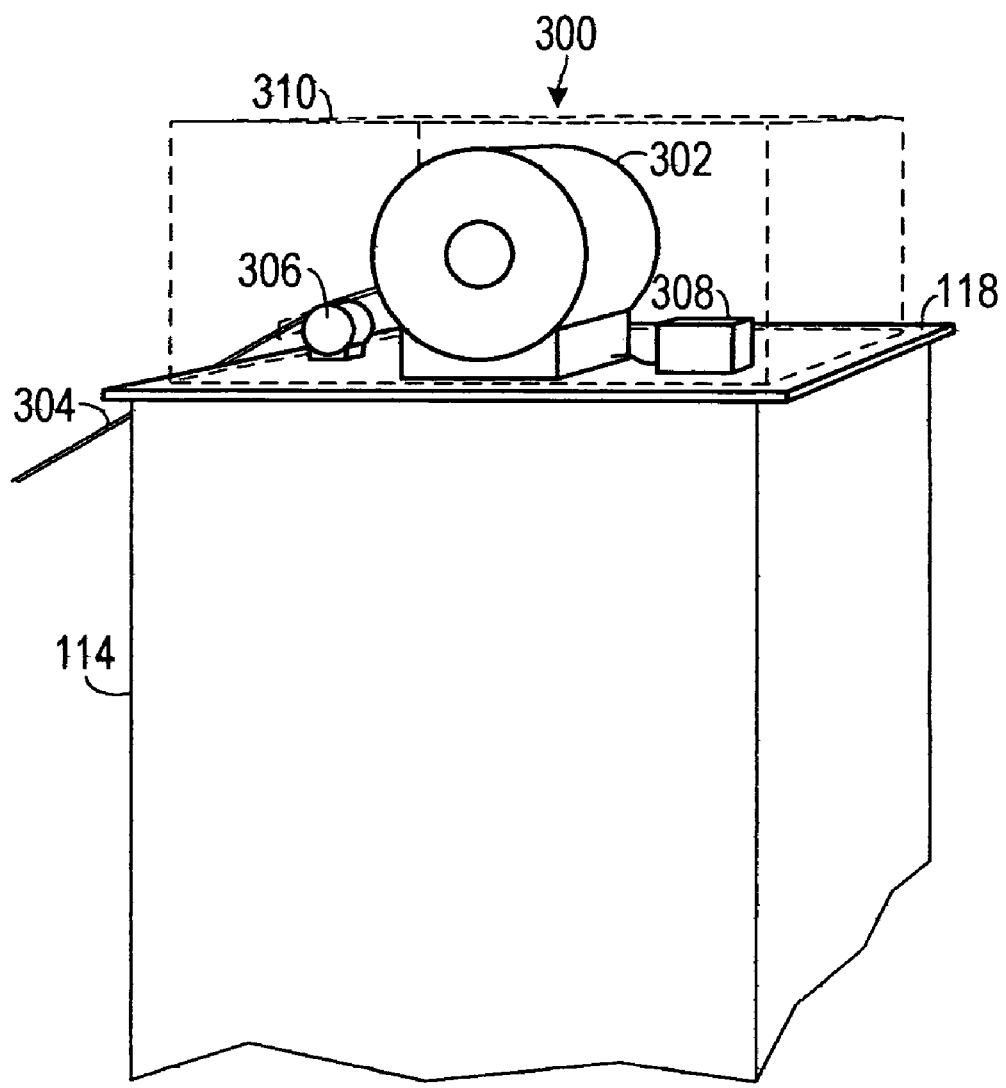
FIG. 3 is a top perspective view of an exemplary distraction head for applying a distraction force to a patient's spine.

FIG. 3 illustrates an exemplary power spinal distraction device 300 for applying a distraction force to a patient's spine. It should be understood that the power distraction device 300 may be mounted on either a top portion of the top member 114 or a side portion of the top member 114. Alternatively, the power distraction device 300 may be mounted to the base 102 or the bottom member 112 and remain fixed and other mechanical devices, such as a pulley, may be coupled to the top member 114 to provide the angular distraction positioning.

The power distraction device 300 may include a motor 302 or other actuator that applies a force to a distraction cable or a strap 304. Other mechanical mechanisms, such as a pulley 306, may be included in the power distraction device 300 for operating the cable 304 by the motor 302. Electronics 308 may be included in the power distraction device 300 to power and/or control the motor 302, thereby controlling the amount of distraction force applied to the patient as part of a treatment profile. The electronics may include a processor for receiving signals from a master computing device (not shown) and convert the signals to motor commands. The electronics may further include motor driving electronics that supply power to the motors 302. Other electrical, electronic, and mechanical components for implementing the functionality of the power distraction device 300 may be included as understood in the art.

In operation, a computing device that controls operation of the top member 114 may be programmed with software or firmware to control operation of the top member 114 dynamically. U.S. Pat. No. 6,152, 950 issued Nov. 28, 2000 provides for various operational concepts and configurations and is herein incorporated by reference. In one embodiment, the vertical extension member 114 may be controlled during treatment of the spine of a patient. For example, once a patient is configured with a harness or other device used to apply force, the vertical extension member 114 may be automatically positioned via a programmed setting to a certain height. If a horizontal pulling force is applied to a patient via a motor other than one operated by the power distraction head 300, then the power distraction head 300 may be synchronously controlled to apply a pulling force. In addition, a third degree-of-freedom may be applied to the treatment by providing for vertical motion of the top member 114 being raised or lowered during the treatment.

In further operation, a distraction angle formed by the cable 304 relative to a bed (not shown) located horizontally perpendicular to the structure 100, may be fixed or varied between zero and thirty degrees to accommodate a flexion over a select area of the lumbar, thereby creating a "rolling" of the lumbar region during a single regiment of distraction types as understood in the art. By creating a rolling flexion, the area of distraction may be moved from a single to multiple disc area. The rolling past a joint may enhance the effect to move the inter-vertebral joint allowing for a more generous treatment area during distraction. By synchronizing the horizontal pulling forces, angular pulling forces, and angular position, three degrees-of-freedom are achieved.

As understood in the art, a variety of pulling forces may be applied to a patient by generating different drive signals. For example, a sinusoidal, square, triangle, or other wave may be used to command motors that are applying pulling forces to a patient for treatment. By being able to adjust the angular distraction automatically, a variety of treatments that have not been able to be performed using conventional distraction equipment may provide doctors and therapists with new treatment programs for patients to alleviate spinal pain.

Figure 4:
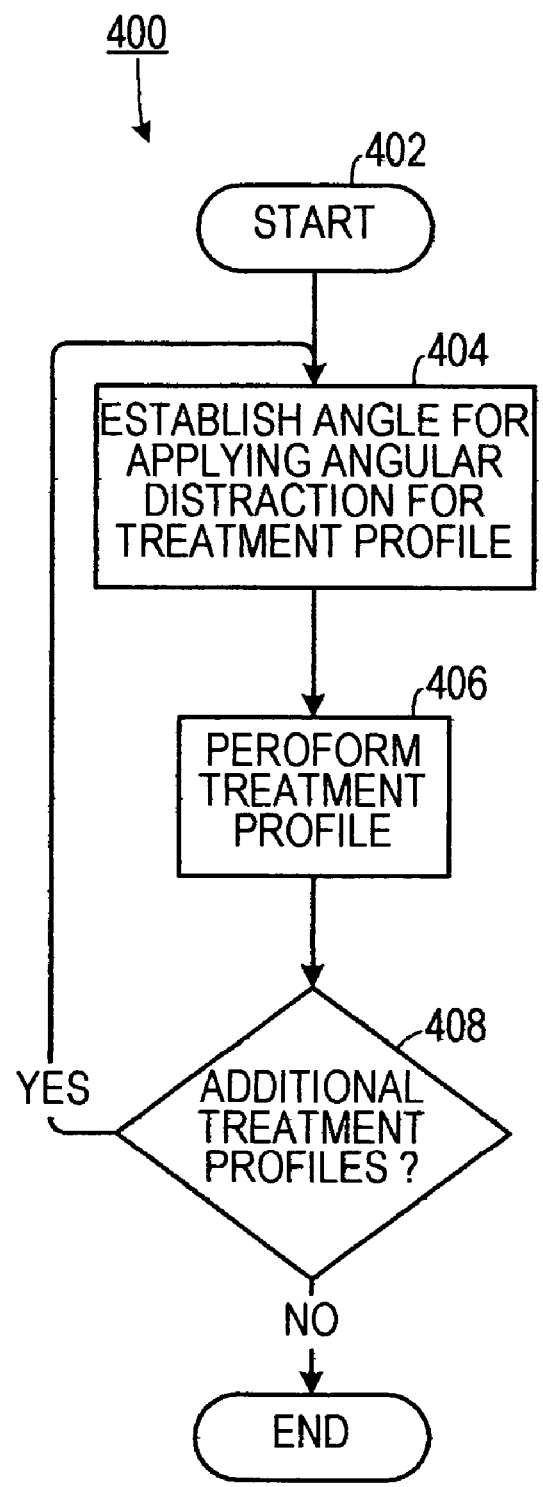
FIG. 4 is a flow chart showing an exemplary method for performing a distraction treatment alerting a vertical distraction angle during spinal treatment.

FIG. 4 illustrates a flow chart setting forth an exemplary method 400 for performing a distraction treatment alerting a vertical distraction angle during spinal treatment. The treatment process starts at step 402 after the patient is configured for a spinal treatment. At step 404, an angle for applying angular distraction for a treatment profile is established. In one embodiment, the top member 114 of FIGS. 1 and 2 are utilized to position a pulling mechanism, such as a cable. A treatment profile to apply pulling forces to a spine of a patient is performed at step 406. The treatment profile may utilize a variety of signaling (e.g., sinusoidal, square, etc.) as understood in the art. During the treatment profile, the distraction angle may remain fixed or be altered. At step 408, a determination if additional treatment profiles may be made. If so, then step 404 is repeated for the new treatment profile. For example, there may be three treatment profiles, one at 10 degrees, one at 20 degrees, and one at 30 degrees. Before each of the profiles, the distraction angle is altered by raising the location of the mechanical element (e.g., cable) extending from the structure 100 for pulling a harness engaging the patient. It should be understood that additional software and control configurations may be utilized in accordance with the present invention.

The structure that integrates components that have traditionally not been configured into a single structure so as to provide a fully integrated piece of equipment that can be integrated, tested, and shipped as a single unit to minimize manufacturing and installation time of the equipment. A single structure may be utilized with substantially any existing bed for performing spinal treatment. One embodiment of the structure includes a base configured to mount a telescoping support. The base may further provide for mounting one or more components, such as electrical (e.g., power supply) or electro-mechanical (e.g., motor) component, utilized to provide spinal treatment. The telescoping support may further be utilized to integrate one or more electrical components (e.g., computing device) for providing spinal treatment. By integrating the components onto a single structure, a manufacturer may functionally test and ship the pedestal without having to fully configure an entire spinal treatment apparatus, including a bed, structure, and equipment that does not configure to the structure as currently performed with conventional spinal treatment equipment.

To overcome the problem of conventional equipment providing for a fixed angular distraction, the principles of the present invention provide for a dynamically alterable vertical adjustment of a structure that provides angular distraction. In one embodiment, the structure is vertically alterable (e.g., telescopic) to raise and lower the distraction angle during treatment. Alternatively, a member of the structure may be externally or internally located such that the height of the pedestal remains fixed while the distraction angle is altered. The structure may be automatically raised and lowered with respect to a predetermined treatment profile that is executed by a computing device supported by the structure.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A spinal treatment apparatus for applying a spinal treatment force to a patient, comprising:
   a. a base portion;
   b. a telescoping support mounted on and extending upwardly from the base portion, the telescoping support including a bottom member and a top member, the top member moveably engaged with the bottom member so that the top member has a retracted position and an extended position, the telescoping support constructed so as to be capable of withstanding a force imparted on the top member, the force corresponding to the spinal treatment force, while in both the retracted position and the extended position;
   c. a spinal distraction device mounted on the top member of telescoping support that applies the spinal treatment force to the patient;
   d. a linear electrical motor that moves the top member vertically relative to the bottom member, thereby moving the spinal distraction device to a selected vertical position;
   e. a treatment bed, capable of supporting the patient, affixed to the bottom member of the telescoping support; and
   f. a counterweight affixed to the bottom member of the telescoping support to balance at least a portion of the force imparted on the top member.

2. The spinal treatment apparatus of claim 1, wherein the bottom member comprises at least one mounting surface to which an equipment is mounted thereto.

3. The spinal treatment apparatus of claim 1, wherein the base portion comprises at least one mounting surface to which equipment is mounted thereto.

* * * * *